United States Patent
Nagl

(10) Patent No.: US 12,171,732 B2
(45) Date of Patent: Dec. 24, 2024

(54) COMPOSITIONS AND USE OF N-CHLOROTAURINE FOR TREATMENT AND PREVENTION OF RESPIRATORY INFECTIONS

(71) Applicant: Markus Nagl, Axams (AT)

(72) Inventor: Markus Nagl, Axams (AT)

(*) Notice: Subject to any disclaimer, the term of this patent is extended or adjusted under 35 U.S.C. 154(b) by 0 days.

(21) Appl. No.: 17/683,197

(22) Filed: Feb. 28, 2022

(65) Prior Publication Data

US 2022/0273594 A1     Sep. 1, 2022

Related U.S. Application Data

(60) Provisional application No. 63/314,641, filed on Feb. 28, 2022, provisional application No. 63/310,535, filed on Feb. 15, 2022, provisional application No. 63/309,460, filed on Feb. 11, 2022, provisional application No. 63/161,498, filed on Mar. 16, 2021, provisional application No. 63/154,758, filed on Feb. 28, 2021, provisional application No. 63/154,430, filed on Feb. 26, 2021.

(51) Int. Cl.
| | | |
|---|---|---|
| *A61K 31/185* | (2006.01) | |
| *A61K 9/00* | (2006.01) | |
| *A61K 9/08* | (2006.01) | |
| *A61P 31/14* | (2006.01) | |

(52) U.S. Cl.
CPC .......... *A61K 31/185* (2013.01); *A61K 9/0043* (2013.01); *A61K 9/006* (2013.01); *A61K 9/0078* (2013.01); *A61K 9/08* (2013.01); *A61P 31/14* (2018.01)

(58) Field of Classification Search
CPC .... A61K 31/185; A61K 9/0043; A61K 9/006; A61K 9/0078; A61K 9/08; A61P 31/14
See application file for complete search history.

(56) References Cited

U.S. PATENT DOCUMENTS

| | | | |
|---|---|---|---|
| 2008/0207750 A1* | 8/2008 | Gottardi | A61P 31/00 514/517 |
| 2011/0151025 A1* | 6/2011 | Gottardi | A61K 31/69 424/720 |
| 2021/0228619 A1* | 7/2021 | Peyman | A61K 9/5036 |

* cited by examiner

*Primary Examiner* — Kara R McMillian
(74) *Attorney, Agent, or Firm* — Frederic P. Zotos, Esq.

(57) ABSTRACT

Composition and methods for treatment or prevention of a respiratory infection in a mammal, including a viral infection, like a coronavirus such as severe acute respiratory syndrome coronavirus 2 (SARS-CoV-2), or variants thereof. The compositions and methods include a therapeutically effective amount of about a 1% solution of N-chlorotaurine in water. The methods include administering N-chlorotaurine by nasal spray to the nostrils, by oral spray to the throat, and by nebulizer to the lungs.

12 Claims, 14 Drawing Sheets

SARS-CoV-2 (hCoV-19/Australia/VIC01/2020)
time [min]

FIG. 1B

UniProtKB - P0DTC2 (SPIKE_SARS2)

```
  MFVFLVLLPL VSSQCVNLTT RTQLPPAYTN SFTRGVYY   PD KVFRSSVLHS   50
  TQDLFLPFFS NVTWFHAIHV SGTNGTKRFD NPVLPFNDGV YFASTEKSNI     100
  IRGWIFGTTL DSKTQSLLIV NNATNVVIKV CEFQFCNDPF LGVYYHKNNK     150
  SWMESEFRVY SSANNCTFEY VSQPFLMDLE GKQGNFKNLR EFVFKNIDGY     200
  FKIYSKHTPI NLVRDLPQGF SALEPLVDLP IGINITRFQT LLALHRSYLT     250
  PGDSSSGWTA GAAAYYVGYL QPRTFLLKYN ENGTITDAVD CALDPLSETK     300
  CTLKSFTVEK GIYQTSNFRV QPTESIVRFP NITNLCPFGE VFNATRFASV     350
  YAWNRKRISN CVADYSVLYN SASFSTFKCY GVSPTKLNDL CFTNVYADSF     400
  VIRGDEVRQI APGQTGKIAD YNYKLPDDFT GCVIAWNSNN LDSKVGGNYN     450
  YLYRLFRKSN LKPFERDIST EIYQAGSTPC NGVEGFNCYF PLQSYGFQPT     500
  NGVGYQPYRV VVLSFELLHA PATVCGPKKS TNLVKNKCVN FNFNGLTGTG     550
  VLTESNKKFL PFQQFGRDIA DTTDAVRDPQ TLEILDITPC SFGGVSVITP     600
  GTNTSNQVAV LYQDVNCTEV PVAIHADQLT PTWRVYSTGS NVFQTRAGCL     650
  IGAEHVNNSY ECDIPIGAGI CASYQTQTNS PRRARSVASQ SIIAYTMSLG     700
  AENSVAYSNN SIAIPTNFTI SVTTEILPVS MTKTSVDCTM YICGDSTECS     750
  NLLLQYGSFC TQLNRALTGI AVEQDKNTQE VFAQVKQIYK TPPIKDFGGF     800
  NFSQILPDPS KPSKRSFIED LLFNKVTLAD AGFIKQYGDC LGDIAARDLI     850
  CAQKFNGLTV LPPLLTDEMI AQYTSALLAG TITSGWTFGA GAALQIPFAM     900
  QMAYRFNGIG VTQNVLYENQ KLIANQFNSA IGKIQDSLSS TASALGKLQD     950
  VVNQNAQALN TLVKQLSSNF GAISSVLNDI LSRLDKVEAE VQIDRLITGR    1000
  LQSLQTYVTQ QLIRAAEIRA SANLAATKMS ECVLGQSKRV DFCGKGYHLM    1050
  SFPQSAPHGV VFLHVTYVPA QEKNFTTAPA ICHDGKAHFP REGVFVSNGT    1100
  HWFVTQRNFY EPQIITTDNT FVSGNCDVVI GIVNNTVYDP LQPELDSFKE    1150
  ELDKYFKNHT SPDVDLGDIS GINASVVNIQ KEIDRLNEVA KNLNESLIDL    1200
  QELGKYEQYI KWPWYIWLGF IAGLIAIVMV TIMLCCMTSC CSCLKGCCSC    1250
  GSCCKFDEDD SEPVLKGVKL HYT
```

| Identified Peptide | Position in Protein | Chlorination / Oxidation Site |
|---|---|---|
| TQLPPAYTNSFT | 22 - 34 | Y 28 |
| GVYYPDK | 35 - 41 | Y 37 |
| GVYYPDK | 35 - 41 | Y 38 |
| GVYYPDK | 35 - 41 | Y 37 and Y 38 |
| GVYYPDKVFR | 35 - 44 | Y 37 |
| GVYYPDKVFR | 35 - 44 | Y 38 |
| GVYYPDKVFR | 35 - 44 | Y 37 and Y 38 |
| SWMESEFR | 151 - 158 | M 153 |
| NIDGYFK | 196 - 202 | Y 200 |

| | | |
|---|---|---|
| SYLTPGDSSSGWTAGAAAYYVGYLQPR | 247 - 273 | Y 248 |
| SFTVEKGIYQTSNFR | 305 - 319 | Y 313 |
| GIYQTSNFR | 311 - 319 | Y 313 |
| FASVYAWNR | 347 - 355 | Y 351 |
| FASVYAWNR | 347 - 355 | Y 351 and W 353 |
| ISNCVADYSVLYNSASFSTFK | 358 - 378 | Y 365 |
| ISNCVADYSVLYNSASFSTFK | 358 - 378 | Y 369 |
| CYGVSPTK | 379 - 386 | Y 380 |
| CYGVSPTKLNDLCFTNVYADSFVIRGDEVR | 379 - 408 | Y 396 |
| LNDLCFTNVYADSFVIR | 387 - 403 | Y 396 |
| LNDLCFTNVYADSFVIRGDEVR | 387 - 408 | Y 396 and F 400 |
| IADYNYK | 418 - 424 | Y 421 |
| IADYNYK | 418 - 424 | Y 423 |
| VGGNYNYLYR | 445 - 454 | Y 449 |
| VGGNYNYLYR | 445 - 454 | Y 451 |
| VGGNYNYLYR | 445 - 454 | Y 453 |
| VGGNYNYLYR | 445 - 454 | Y 449 and Y 451 |
| VGGNYNYLYR | 445 - 454 | Y 451 and Y 453 |
| VYSTGSNVFQTR | 635 - 646 | Y 636 |
| SFIEDLLFNKVTLADAGFIKQYGDCLGDIAAR | 816 - 847 | F 833 and Y 837 |
| QYGDCLGDIAAR | 836 - 847 | Y 837 |
| FNGIGVTQNVLYENQK | 906 - 921 | Y 917 |
| ASANLAATKMSECVLGQSKR | 1020 - 1039 | M 1029 |
| ASANLAATKMSECVLGQSK | 1020 - 1038 | M 1029 |
| MSECVLGQSKRVDFCGK | 1029 - 1045 | M 1029 |
| MSECVLGQSKR | 1029 - 1039 | M 1029 |
| MSECVLGQSK | 1029 - 1038 | M 1029 |

FIG. 4

1041  3C-like proteinase

1042  SGFRKMAFPS GKVEGCMVQV TCGTTTLNGL WLDDVVYCPR HVICTSEDML  50
1043  NPNYEDLLIR KSNHNFLVQA GNVQLRVIGH SMQNCVLKLK VDTANPKTPK  100
1044  YKFVRIQPGQ TFSVLACYNG SPSGVYQCAM RPNFTIKGSF LNGSCGSVGF  150
1045  NIDYDCVSFC YMHHMELPTG VHAGTDLEGN FYGPFVDRQT AQAAGTDTTI  200
1046  TVNVLAWLYA AVINGDRWFL NRFTTTLNDF NLVAMKYNYE PLTQDHVDIL  250
1047  GPLSAQTGIA VLDMCASLKE LLQNGMNGRT ILGSALLEDE FTPFDVVRQC  300
1048  SGVTFQ

| Identified Peptide | Position in Protein | Chlorination Site | Oxidation Site | | |
|---|---|---|---|---|---|
| | | | Mono | Di | Tri |
| KMAFPSGK | 5 – 12 | - | M6 | M6 | - |
| HVICTSEDMLNPNYEDLLIR | 41 – 60 | Y54 | M49 | M49, C44 | C44 |
| KSNHNFLVQAGNVQLR | 61 – 76 | H64 | - | - | - |
| VIGHSMQNCVLK | 77 – 88 | H80 | M82 | M82, C85 | C85 |
| VDTANPKTPKYK | 91 – 102 | Y101 | - | - | - |
| IQPGQTFSVLACYNGSPSG VYQCAM RPNFTIK | 106 – 137 | - | M130 | - | C117 |
| QTAQAAGTDTTITVNVLA WLYAAVINGDRWFLNR | 189 – 222 | Y209 | - | - | - |
| FTTTLNDFNLVAMK | 223 – 236 | - | M235 | M235 | - |
| YNYEPLTQDHVDILGPLSAQ TGIAVLDMCASLK | 237 – 269 | - | M264 | - | - |
| ELLQNGMNGR | 270 – 279 | - | M276 | - | - |
| QCSGVTFQ | 299 – 306 | - | - | C300 | C300 |

FIG. 5

COMPOSITIONS AND USE OF N-CHLOROTAURINE FOR TREATMENT AND PREVENTION OF RESPIRATORY INFECTIONS

CROSS-REFERENCE TO RELATED APPLICATIONS

This application claims priority to U.S. Provisional Applications Nos. 63/154,430 filed on Feb. 26, 2021, 63/154,758 filed on Feb. 28, 2021, 63/161,498 filed on Mar. 16, 2021, 63/309,460 filed on Feb. 11, 2022, 63/310,535 filed on Feb. 15, 2022, and 63/314,641 filed on Feb. 28, 2022, the entire contents all of which are hereby incorporated by reference.

FIELD

This invention relates to antimicrobial, anti-infective and antiseptic compositions and methods for the treatment and prevention of respiratory infections. More particularly, this invention relates to the use of N-chlorotaurine compositions and methods for the treatment and prevention of respiratory infections in mammals, particularly humans.

BACKGROUND

Infections are a permanent problem in human medicine. Airway infections including bronchitis and pneumonia are mostly caused by viruses and bacteria, but in the last decades also fungal infections have been increasing mainly due to immunosuppressive drugs which are used to treat cancer.

Many antibiotics are available to treat bacterial infections, and fewer drugs to treat viral and fungal infections. A problem with antibiotics, particularly with antiviral and antifungal drugs, is antimicrobial resistance. Some bacteria contain multidrug resistance genes and can be treated successfully only with a few available antibiotics. Recently, such genes have been found in fungi too, and a significant number of immunosuppressed patients die from fungal infections which are acquired through the airway route. To date, only a few viruses can be treated with specific antiviral agents.

Antiseptics are active against a broad-spectrum of pathogens usually including all mentioned classes of pathogens. If antiseptics are used in sufficient concentrations, acquired resistance (i.e., resistance which develops during repeated application of the same substance) does not occur. This is due to the unspecific reaction mechanism of most antiseptics, and is an advantage above antibiotics. However, antiseptics are much more toxic than antibiotics so that they cannot be applied systemically (i.e., intravenously, orally, intra-arterially). Only topical application to skin and mucous membranes is possible. There are delicate locations where not all antiseptics can be applied, e.g., the eye, body cavities such as paranasal sinuses, and the urinary bladder.

Special areas are the deeper airways, particularly the bronchopulmonary system, consisting of bronchi, bronchioli, and alveoli. Antiseptics are not used upon inhalation since significant concentrations are not tolerated because of irritative or toxic reactions, or considerable systemic resorption (e.g., alcohols, iodine). For instance, chloramine T has been shown to cause asthmatic and inflammatory symptoms after inhalative application.

Therefore, new compositions are needed for the treatment of infections of the bronchopulmonary system which can be applied topically, have sufficient activity against the causative pathogens, do not induce resistance of the pathogens, and are well tolerated upon inhalation.

Recently, the coronavirus disease 2019 (COVID-19) pandemic has been the major challenge for human health in this 21st century. The COVID-19 pandemic is caused by SARS-CoV-2. The pandemic is affecting individuals, populations, and health systems far beyond infection. The virus might persist globally and become a prolonged or permanent threat. The race for a cure is a global effort and different approaches have been proposed and are currently studied.

Another major public concern is posed by influenza viruses, which annually cause 3-5 million cases of severe illness and about 290,000 to 650.000 of death worldwide. Protection by the yearly influenza virus vaccine is unsatisfactory and resistance against existing antiviral drugs develops rapidly. Therefore, new tools to combat influenza viruses are urgently needed.

One less known intervention is inhalation therapy with antiviral agents. A first advantage is direct delivery of a high concentration of the medication to the lung, where the virus causes most of the severe problems. Furthermore, topically applied therapies that are not systemically distributed avoid interactions with systemic medications, which are frequently necessary in elderly or multimorbid patients who are particularly at risk for severe COVID-19 complications. An ideal inhaled drug should have broad-spectrum antimicrobial activity to cover not only SARS-CoV-2, but also co-infections and superinfections with other respiratory viruses and microorganisms (bacteria and fungi).

Antiviral drugs are often specific to distinct viruses, but identifying the virus causing an infection requires logistic and diagnostic efforts, which in the case of SARS-CoV-2 amounts to at best one to two days for a diagnosis. Such an ideal inhaled broad-spectrum drug mentioned above could be applied instantly regardless of the pathogen causing the respiratory illness and would thus eliminate the need for time-consuming diagnostics.

Another key requirement is anti-inflammatory activity of the compound to downregulate the "cytokine storm", particularly for SARS-CoV-2, which causes hyper-inflammation in severe cases.

A safe, well tolerated, endogenous, inhaled substance with broad-spectrum activity against pathogens supported by anti-inflammatory properties may be a significant step forward for treatment of COVID-19 and other viral infections of the lower airways without the need of further diagnostics to discriminate between the infectious agents.

Therefore, highly sufficient and well tolerated medications for therapy and prophylaxis of respiratory infections, including COVID-19 and influenza viruses, are urgently needed.

SUMMARY

In one aspect of the invention, there is provided a composition for treatment or prevention of a respiratory infection in a mammal, the composition comprising a therapeutically effective amount of N-chlorotaurine.

In various embodiments, the respiratory infection is a viral infection, like a coronavirus, including severe acute respiratory syndrome coronavirus 2 (SARS-CoV-2), or variants thereof.

In various embodiments, the composition of a therapeutically effective amount of N-chlorotaurine comprises about a 0.1% to 1% solution of N-chlorotaurine in water.

In another aspect, there is provided a method of treating or preventing a respiratory infection in a mammal, the method comprising administering a therapeutically effective amount of N-chlorotaurine.

In one embodiment, the method of administering a therapeutically effective amount of N-chlorotaurine comprises administration by nasal spray to the nostrils. The therapeutically effective amount of N-chlorotaurine comprises a dosage of about 0.1 ml to 0.3 ml per administration to each of the nostrils, administered about 2 to 4 times per day.

In another embodiment, the method of administering a therapeutically effective amount of N-chlorotaurine comprises administration by oral spray to the throat. The therapeutically effective amount of N-chlorotaurine comprises a dosage of about 0.3 ml to 0.6 ml per administration to the throat, administered about 2 to 4 times per day.

In another embodiment, the method of administering a therapeutically effective amount of N-chlorotaurine comprises administration by inhalation by nebulizer to the lungs. The therapeutically effective amount of N-chlorotaurine comprises a dosage of about 2 ml to 5 ml per administration to the lungs, administered about 2 to 4 times per day.

It is understood that any aspect, feature, or embodiment of the invention can be combined with any other aspect, feature or embodiment of the invention, without departing from the scope of the invention. Other aspects and advantages of the invention will become apparent from the following description and claims.

BRIEF DESCRIPTION OF THE FIGURES

FIG. 1B presents inactivation of SARS-Cov-2 (hCoV-19/Australia/VIC01/2020) by NCT. Virus suspension (SARS-CoV-2 h CoV-19/Australia/VIC01/2020) was incubated with NCT or PBS or isopropanol (positive control) for 5 min, 10 min, 20 min, and 60 min at 37° C. and then diluted 1:1 in met/his for inactivation of NCT, followed by plaque titration. Mean values±SD of three independent experiments. Detection limit 3.11 log10 (dotted line).

FIGS. 4A and 4B present chlorination of tyrosines, phenylalanines and tryptophan and oxidation of methionine of SARS-CoV-2 spike protein by NCT. Spike protein was incubated for 30 min at 37° C. in 1% NCT and subjected to mass spectrometry. Positions of chlorinated and oxidized amino acids in the sequence are shown, with 18 tyrosines, two phenylalanines, and one tryptophan chlorinated and two methionines oxidized. No oxidation was found on cysteine.

FIG. 5 presents Chlorination of tyrosines and histidines and oxidation of methionines and cysteines of SARS-CoV-2 3C-like proteinase by NCT. Proteinase was incubated for 30 min at 37° C. in 1% NCT and subjected to mass spectrometry. Positions of chlorinated and oxidized amino acids in the sequence are shown, with 3 tyrosines and two histidines chlorinated and seven methionines and four cysteines oxidized.

DETAILED DESCRIPTION

Figure 1A:
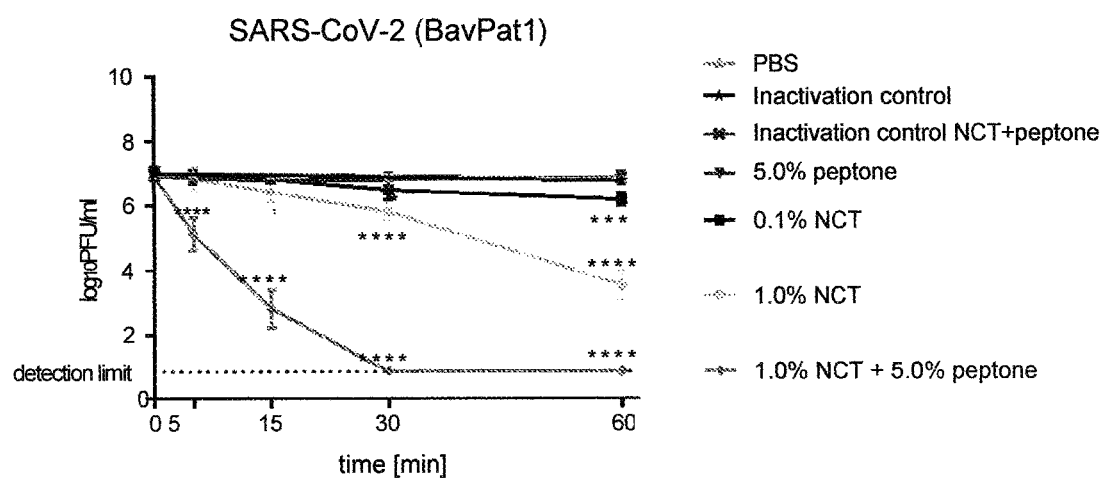
FIG. 1A presents inactivation of SARS-Cov-2 (BAvPat1) by NCT. Virus suspension (SARS-CoV-2 BavPat1) was incubated with 1.0% (55 mM) NCT, 0.1% (5.5 mM) NCT, 1.0% NCT with 5.0% peptone or PBS or 5.0% peptone for 5 min, 15 min, 30 min, or 60 min at 37° C., after which samples were diluted 1:1 in met/his solution for inactivation of NCT. Remaining infectious virus particles were determined using plaque titration. To control for inactivation of NCT by met/his, virus was added after dilution of 1.0% NCT with or without peptone in met/his. Mean values±SD of three to eight independent experiments in duplicates. The dotted line indicates the detection limit (0.84 log10). Data were statistically analyzed using a two-way ANOVA including a Dunnett's multiple comparison test to PBS controls. $*p<0.05$, $p<0.01$, $*p<0.001$, $****p<0.0001$. Of note, the inactivation of the virus by NCT was markedly enhanced in the presence of peptone.

The invention, in all of its various aspects and embodiments, comprises N-chlorotaurine (Cl—NH—CH2-CH2-SO3-) in compositions, devices, methods, and/or uses having antimicrobial properties in mammals, particularly humans.

N-chlorotaurine (Cl—NH—CH2-CH2-SO3-) is a small molecule that fulfils the criteria of broad-spectrum antimicrobial (virucidal, bactericidal, fungicidal, protozoocidal) and anti-inflammatory activity, and good tolerability upon inhalation. It is the product of activated human granulocytes and monocytes and belongs to the long-lived oxidants and chloramines formed by the myeloperoxidase via hypochlorous acid to combat invading pathogens. Moreover, N-chlorotaurine is thought to be involved in the control of inflammation by downregulating of nuclear factor kappaB activation, chemokines and proinflammatory cytokines such as tumor necrosis factor alpha, some prostaglandins and interleukins like IL-6.

The synthesis of the sodium salt of N-chlorotaurine (Cl—NH—CH2-CH2-SO3Na, NCT) is successful in the laboratory, which enables its development as an endogenous anti-infective and mild antiseptic in human medicine. Suitable salts can be prepared by known methods, including but not limited to the method described in German Patent Application 4041703, filed on Dec. 24, 1990, by Gottardi (incorporated by reference herein in its entirety).

As an active chlorine compound belonging to the class of chloramines, NCT has the broad-spectrum microbicidal activity without development of resistance against Gram-positive and Gram-negative bacteria including multi-resistant strains, yeasts and moulds, protozoa, and worm larvae. Broad-spectrum activity is found against adenoviruses, herpes viruses 1 and 2, human immunodeficiency virus, and is shown in vivo against adeno and herpes viruses in epidemic keratoconjunctivitis up to a phase II study as well as in herpes zoster in a case report, respectively. Activity against coxsackievirus A24 and enterovirus 70 is found by the NCT-derivative N,N-dichloro-dimethyltaurine in vitro.

Inhalation of NCT is being investigated and developed. NCT demonstrates enhanced bactericidal and fungicidal activity in the presence of lung epithelial cells. Tolerability of repeatedly inhaled NCT is confirmed in the normal lung and in a streptoccoccal inflammation model each in pigs, and in the normal lung of mice. In humans, tolerability is confirmed in a placebo-controlled phase I clinical study. Only minor and transient adverse effects were found, i.e. chlorine taste and occasional tickle in the throat. NCT is not distributed systemically, which explains the absence of systemic adverse effects.

In one embodiment of the invention, the alkali salt of N-Chlorotaurine (NCT), preferably the sodium salt, is used in the treatment and prophylaxis of a viral respiratory infection in a mammal, especially an infection of the lungs, the airways of the lower respiratory tract leading thereto, the upper respiratory tract, the nasal cavity, the oral cavity, or the throat. Examples of such viral infections include severe acute respiratory syndrome coronavirus 2 (SARS-CoV-2), respiratory syncytial virus (RSV), influenza viruses (Influenza A or B virus), or derivatives thereof.

In Vitro

NCT was incubated with SARS-CoV-2, influenza A virus or RSV, followed by assessment of virus inactivation using various readouts. NCT at a clinically relevant concentration of 0.1%-1.0% demonstrated virucidal activity against SARS-CoV-2 (SARS-CoV-2 BavPat1, hCoV-19/Australia/VIC01/2020, clinical isolate 1.2 Innsbruck from early 2020, as well as the B.1.1.7 (Alpha) and B.1.351 (Beta) variants of concern, influenza A virus, and RSV (RSV long strain). Longer NCT-exposure periods were required to inactivate SARS-CoV-2 than to inactivate influenza viruses or RSV. In the presence of organic matter, inactivation of viruses was even enhanced so that a significant reduction of plaque forming units and infected cells, respectively, could be observed already after 5 min with SARS-CoV-2 by 1.0% NCT. Controls without NCT and specific inactivation controls showed full viral replication in all cases to warrant valid results. The multiplicity of target sites for NCT, which excludes the acquisition of distinct resistance mutations, was exemplarily demonstrated by mass spectrometry analysis of NCT-treated spike protein of SARS-CoV-2. Detailed results are presented in the following paragraphs.

Virucidal Activity of NCT Against SARS-CoV-2

Inactivation of SARS-CoV-2 wild type isolates from early 2020 was assessed by incubating stock virus with NCT for indicated time periods at 37° C. and then determining the remaining infectious particles using plaque assay or immunostaining as well as determining virus inactivation via RT-qPCR or TCID50. Exact incubation times of virus with NCT were ensured by adding met/his at the end of the incubation period, which inactivates NCT. All assays demonstrated a significant inactivation of SARS-CoV-2 with slight differences according to the individual test method and strain used.

Figure 1B:
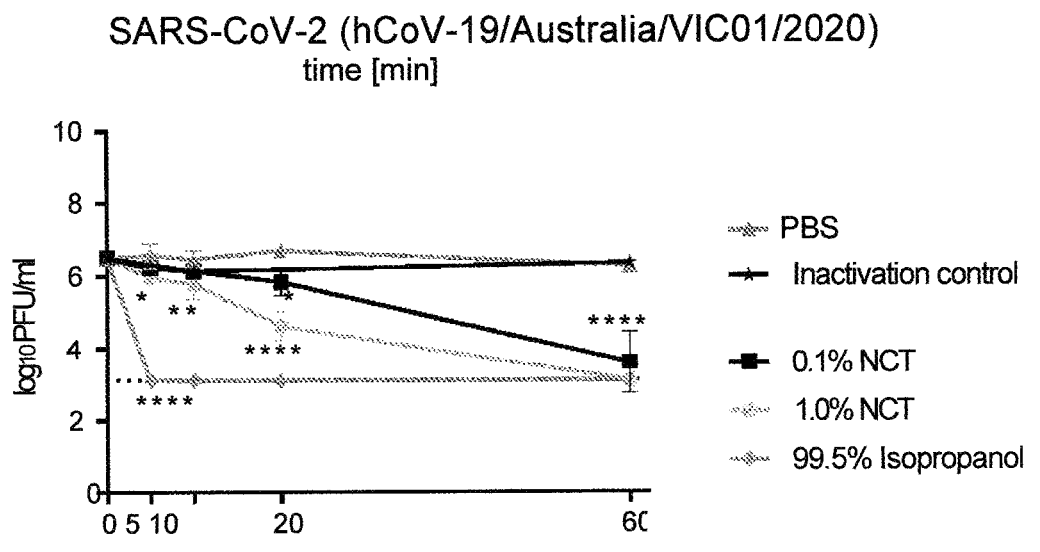

With plaque assay readout, a significant reduction in infectious particles was detected after 15 min of incubation, when incubating SARS-CoV-2 with NCT in a buffered aqueous solution (FIG. 1A). The mild oxidizing activity of the test antiseptic may explain why it took as long as 15 min to reduce infectious particles. In the presence of Vero cells (FIG. 1B) or particularly 5.0% peptone (FIG. 1A), however, a significant reduction of infectious virus particles occurred already after 5 min of incubation with 1.0% NCT. This remarkable enhancement of activity for NCT by organic load is shown for viruses for the first time here and is explained most likely by transhalogenation.

Figure 1C:
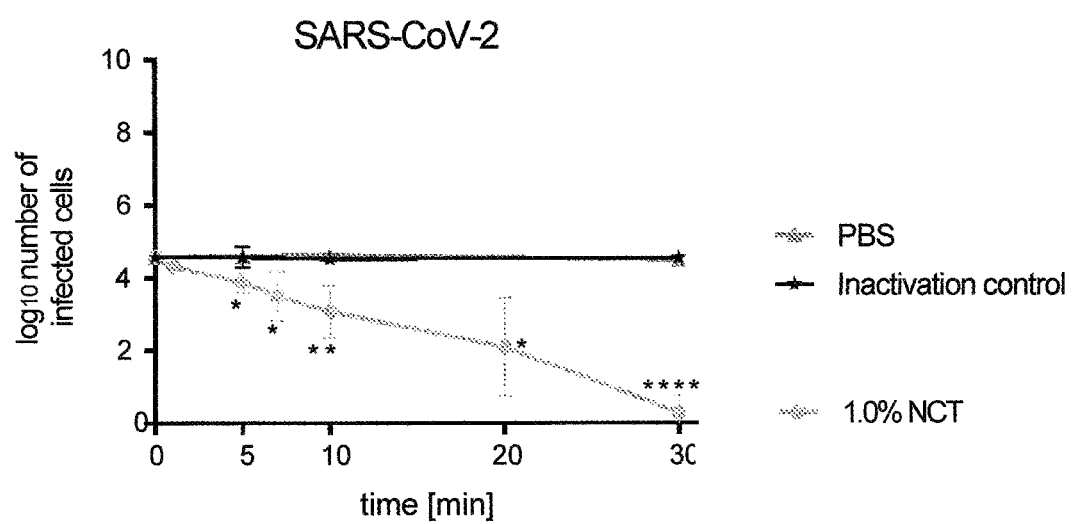
FIG. 1C presents inactivation of SARS-Cov-2 (SARS-CoV-2, clinical isolate) by NCT. Virus suspension (SARS-CoV-2, clinical isolate) was incubated with 1% NCT or PBS for 1 min, 5 min, 7 min, 10 min, 20 min, and 30 min at 37° C. After inactivation of NCT and serial dilution, aliquots were added to Vero/TMPRSS2/ACE2 cells for 1 h in 96-well plates. Cells were washed, incubated for further 9 h, and fixed for Immunostaining (c) or RT-qPCR (d). In immunostaining, infected cells were visible as red spots and counted using an ImmunoSpot S6 Ultra-V reader and CTL analyser BioSpot® 5.0 software. Mean values±SD of three independent experiments.
Figure 1D:
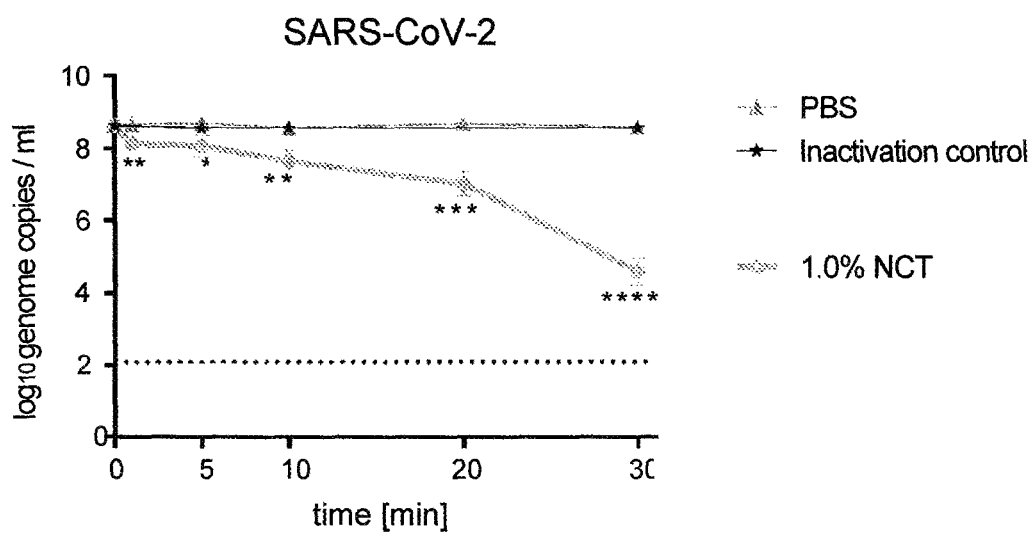
FIG. 1D presents inactivation of SARS-Cov-2 by NCT. After cell lysis and RNA extraction, one-step RT-qPCR assay was performed using the iTaq™ RT-PCR (BIO-RAD) kit and previously published primers and probes specific for detection of the SARS-CoV-2 E Gene on a CFX96™ real-time system (BIO-RAD). Mean values±SD of genome copies of three independent experiments. Detection limit 2.10 log10 RNA copies/ml (dotted line).
Figure 1E:
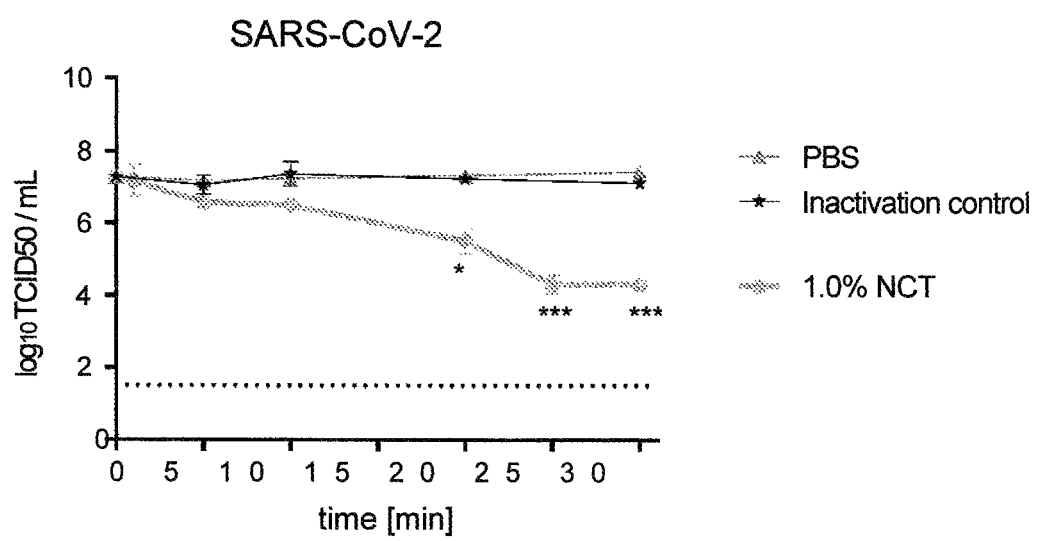
FIG. 1E presents inactivation of SARS-Cov-2 by NCT. Virus titration by TCID50. Mean values±SD of two independent experiments. Detection limit 1.50 log10 (dotted line).

Virus inactivation assays with immunostaining readout showed a 50% reduction of infected cells after 1 min (not significant, p=0.085), 20-80% reduction after 5 min (p=0.0102), 81-91% after 7 min (p<0.01), 81-97% after 10 min, 96-99% after 20 min, and >99% after 30 min (p<0.0001 for these values). A logarithmic scale with respective statistics is provided in FIG. 1C. The results found by RT-qPCR assay were similar with a highly significant reduction of genome copies (FIG. 1D). This was further confirmed by the TCID50 readout (FIG. 1E).

Figure 1F:
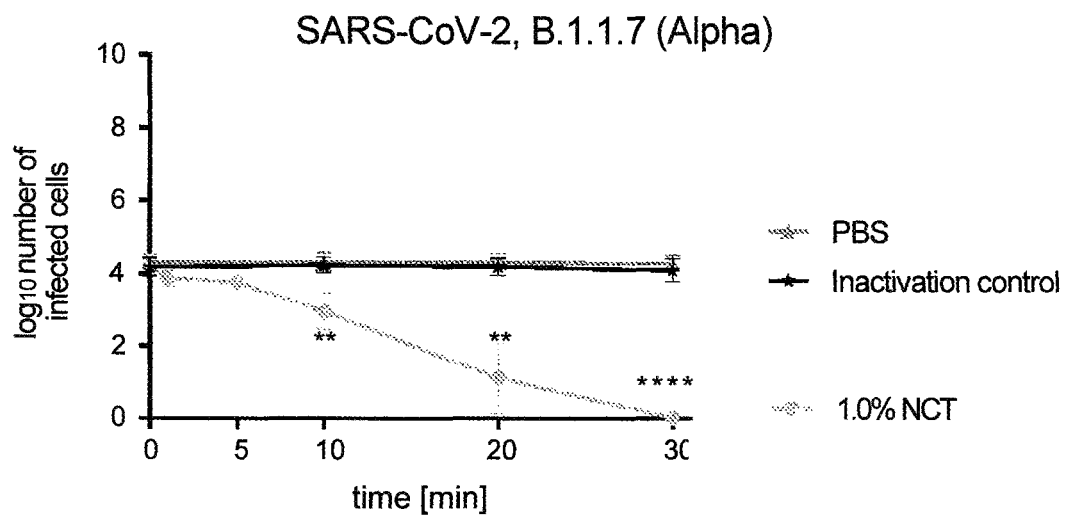
FIGS. 1F and 1G present inactivation of SARS-Cov-2 (variants, i.e. B.1.1.7 (Alpha) (FIG. 1F), B.1.351 (Beta) (FIG. 1G)) by NCT. Virus suspension (SARS-CoV-2 variants, i.e. B.1.1.7 (Alpha) (FIG. 1F), B.1.351 (Beta) (FIG. 1G)) was incubated with 1% NCT or PBS for 1 min, 5 min, 10 min, 20 min, and 30 min at 37° C. After inactivation of NCT and serial dilution, aliquots were added to Vero/TMPRSS2/ACE2 cells for 1 h in 96-well plates. Cells were washed, incubated for further 9 h, and fixed for Immunostaining. Infected cells were visible as red spots and counted using an ImmunoSpot S6 Ultra-V reader and CTL analyser BioSpot® 5.0 software. Mean values±SD of three independent experiments.
Figure 1G:
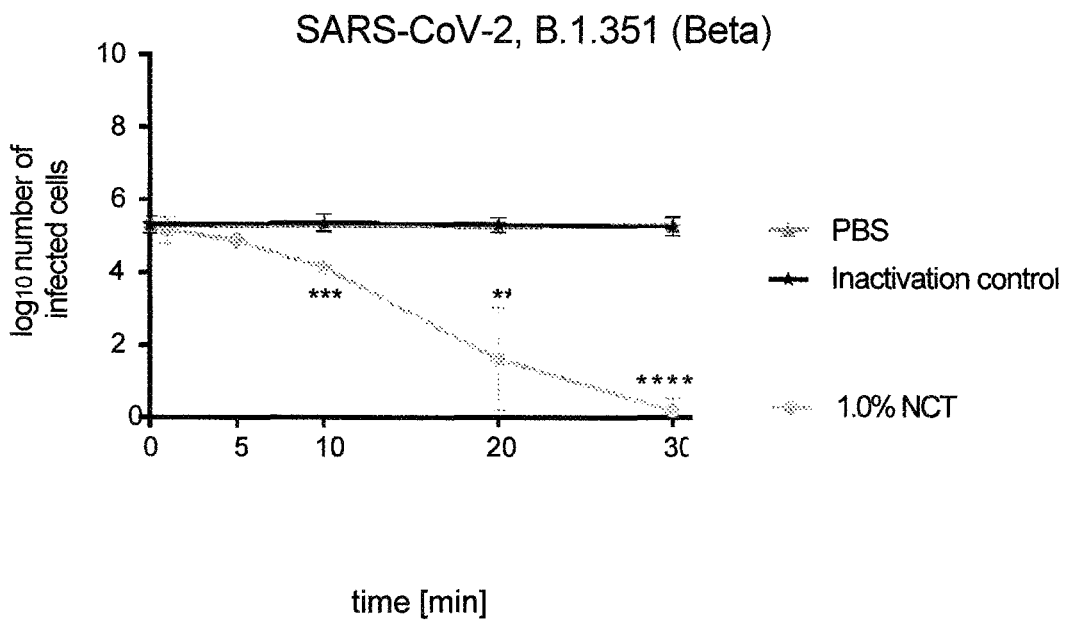

The representative isolates of SARS-CoV-2 variants of concern B.1.1.7 and B.1.351 tested in the virus inactivation assay with immunostaining showed the same susceptibility to NCT than wild type isolates (FIGS. 1F and 1G). For the B.1.1.7 variant, the reduction of infected cells was 42-54% after 1 min (p=0.0109), 50-71% after 5 min (p<0.01), 62-99% after 10 min (p<0.01), 99-100% after 20 min (p<0.001), and 100% after 30 min (p<0.001). The values for the B.1.351 variant were 0-48% after 1 min (not significant, p=0.313), 54-72% after 5 min (p<0.01), 82-97% after 10 min (p<0.001), 99-100% after 20 min (p<0.001), and 100% after 30 min (p<0.001).

The antiviral activity was concentration-dependent. Inactivation controls demonstrated full inactivation of 1.0% NCT by 1.0% methionine/1.0% histidine (met/his). This was valid for all tests and viruses in this study. Absence of cytotoxicity of inactivated NCT to the inoculated cell culture was proved by MTT testing with values of MTT reduction of 94.1±8.5 (0.1% NCT plus 0.1% met/his) and 100.3±5.6 (PBS control) (p=0.12 by Student's unpaired t-test).

Virucidal Activity of NCT Against Influenza Viruses

Figure 2A:
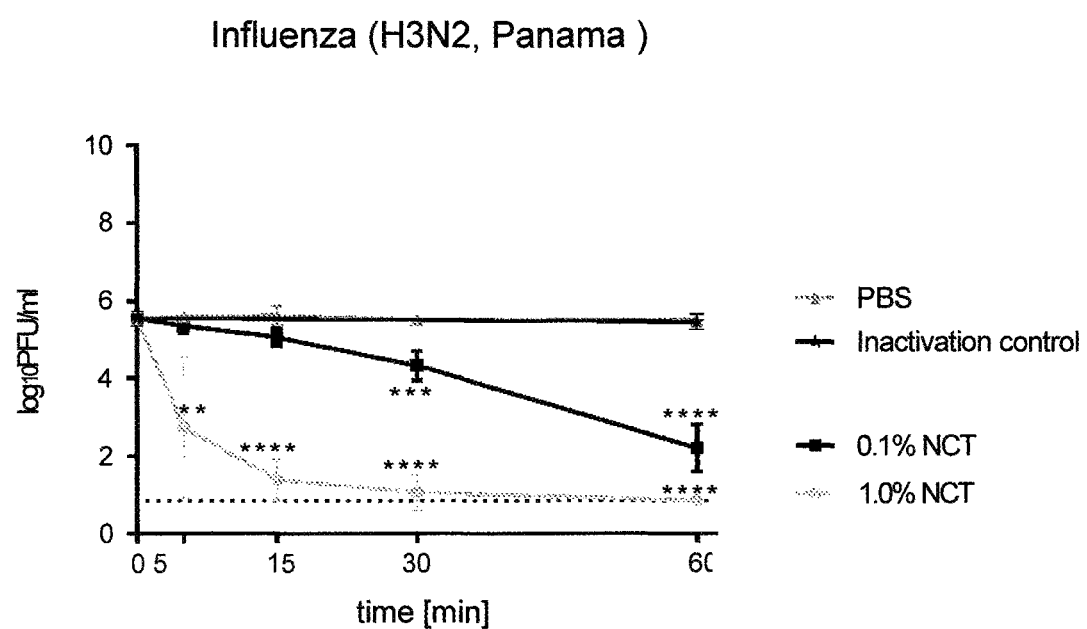
FIG. 2A presents inactivation of Influenza A/Panama/2007/1999 (H3N2) virus by 1.0% (55 mM) and 0.1% (5.5 mM) NCT. Virus suspension was incubated with NCT or PBS for 5 min, 15 min, 30 min, or 60 min at 37° C., after which samples were diluted 1:1 in met/his solution for inactivation of NCT. Remaining infectious virus particles were determined using plaque titration. To control for inactivation of NCT by met/his, virus was added after dilution of 1.0% NCT in met/his in the inactivation control. Mean values±SD of five independent experiments. $*p<0.05$, $p<0.01$, $*p<0.001$, $****p<0.0001$ versus PBS control. Detection limit 0.84 log10 (dotted line).
Figure 2B:
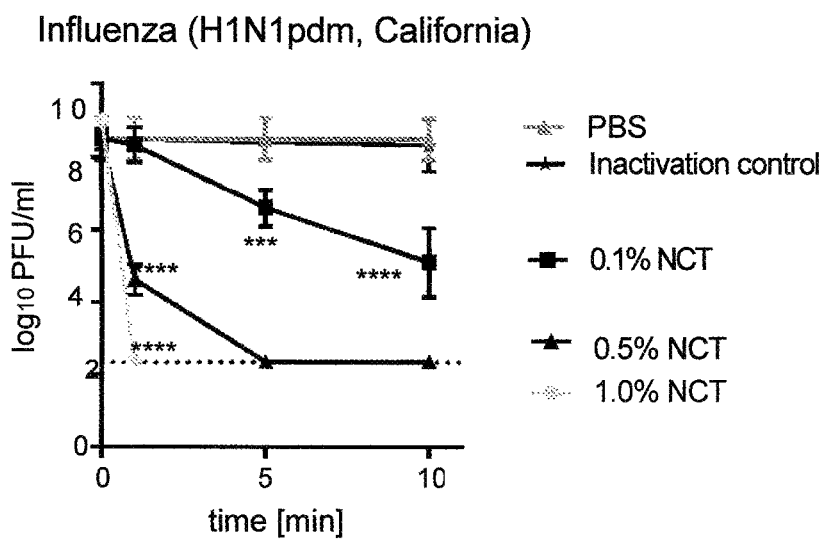
FIG. 2B presents inactivation of Influenza A/California/Swine Origin Virus/2009 (H1N1pdm) virus by 0.1%, 0.5% and 1.0% NCT. Virus suspension was incubated with NCT in RPMI or plain RPMI for 1 min, 5 min, and 10 min at 22° C., after which samples were diluted 1:1 in met/his solution for inactivation of NCT. Remaining infectious virus particles were determined using plaque titration. Mean values±SD of four independent experiments. Detection limit 2.35 log10 (dotted line).
Figure 2C:
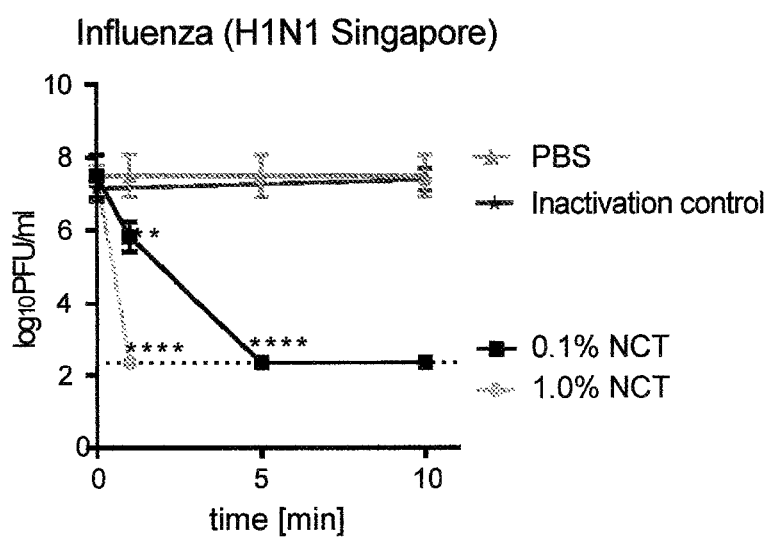
FIG. 2C presents inactivation of Influenza A/Singapore/Hongkong/2339/2000 (H1N1) by 0.1% and 1.0% NCT. Test procedure and number of independent experiments as in FIG. 2B.
Figure 2D:
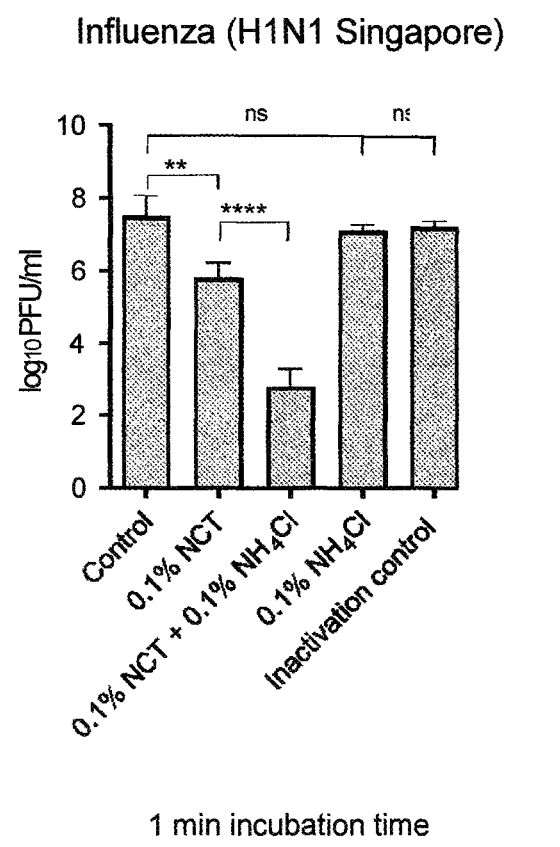
FIG. 2D presents inactivation of Influenza A/Singapore/Hongkong/2339/2000 (H1N1) by 0.1% and 1.0% NCT and by 0.1% NCT and 0.1% (5.5 mM) NCT plus 0.1% (18.7 mM) ammonium chloride compared. Test procedure and number of independent experiments as in FIG. 2B. Inactivation control in (FIG. 2D) consisting of 0.1% NCT plus 0.1% NH4Cl plus inactivator.

Inactivation of influenza viruses was assessed like inactivation of SARS-CoV-2 by incubating stock virus with NCT for indicated time periods at 37° C. and then determining the remaining infectious particles using plaque assay. Virus inactivation as determined by plaque assay readout demonstrated an even faster inactivation of influenza viruses by NCT compared to SARS-CoV-2. All tested virus strains were inactivated rapidly with a 2 log10 reduction of the H3N2 virus within 5 min (FIG. 2A) and a 6 log10 reduction of H1N1 and H1N1pdm viruses within 1 min by 1.0% NCT (FIG. 2B and 2C). In general, H1N1 and H1N1pdm viruses were more susceptible than the H3N2 virus. Addition of ammonium chloride (NH4Cl) to NCT significantly enhanced its activity against influenza viruses (FIG. 2D). Ammonium chloride alone and the inactivation control with 0.1% NCT plus 0.1% ammonium chloride showed no antiviral effect at least up to 10 min incubation time.

Virucidal Activity of NCT Against RSV

Figure 3:
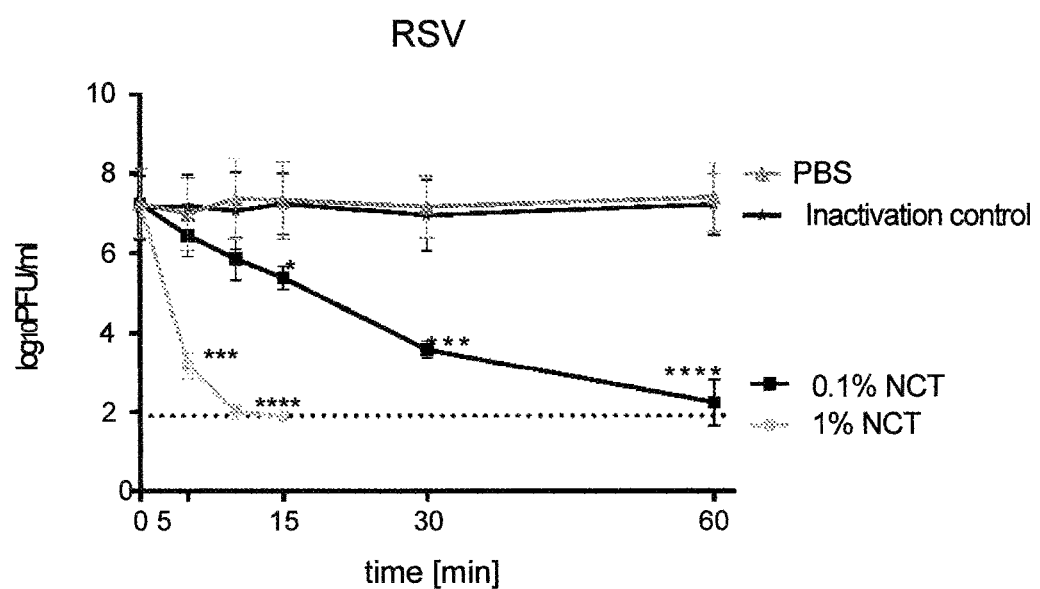
FIG. 3 presents inactivation of respiratory syncytial virus by NCT. Virus suspension was incubated with 1.0% or 0.1% NCT or PBS for 5 min, 10 min, 15 min, 30 min, or 60 min at 37° C., after which samples were diluted 1:1 in met/his solution for inactivation of NCT. Remaining infectious virus particles were determined using plaque titration. Mean values±SD of three independent experiments. Detection limit 1.90 log10 (dotted line).

Inactivation of RSV was assessed as described for SARS-CoV-2 and influenza A viruses. As with SARS-CoV-2 and influenza A virus, inactivation of RSV as determined by plaque assay readout demonstrated a significant reduction of PFU/ml by NCT compared to mock treated controls. The incubation of RSV with 1.0% NCT resulted in a rapid drop of infectious virus titre with 4 log10 decrease within 5 minutes (FIG. 3). Almost no detectable amount of infectious RSV was measurable after 15 minutes. In the presence of 0.1% NCT, RSV titres dropped in a time- and concentration-dependent manner reaching significant titre reduction after 15 minutes (FIG. 3).

Structural Changes of Coronavirus SARS-CoV-2 Spike Protein by NCT Evaluated by Mass Spectrometry Multiple sites of oxidative attack by NCT could be demonstrated by mass spectrometry. Chlorination of aromatic amino acids was found, in detail of 18 tyrosines, two phenylalanines, and one tryptophan. Two methionines were oxidized. The exact positions of the chlorinated and oxidized amino acids are illustrated in FIG. 4. No oxidation of cysteine could be detected.

Structural Changes of Coronavirus 3C-Like Proteinase by NCT Evaluated by Mass Spectrometry As with spike protein, multiple sites of oxidative attack by NCT could be demonstrated. Chlorination of aromatic amino acids was found, in detail of 3 tyrosines, and two histidines. Seven methionines and four cysteines were oxidized. The exact positions of the chlorinated and oxidized amino acids are illustrated in FIG. 5.

Discussion. NCT has clear virucidal activity against three enveloped RNA viruses highly relevant for infections of the bronchopulmonary system. Depending on the NCT-concentration and test conditions, a rapid reduction of the number of infectious virus particles by several powers of ten within 1-10 minutes is achieved. Influenza A viruses of pre-pandemic and pandemic H1N1 subtype (H1N1 and H1N1pdm) were the most sensitive ones with reduction to the detection limit by 1.0% NCT within 1 min, followed by RSV, influenza (H3N2), and SARS-CoV-2. These differences can be explained by individual dynamics of oxidation and chlorination of proteins of the viral surface, and of penetration of NCT and attack on the viral nucleocapsid proteins. All these target sites have been shown with the NCT analogue N,N-dichloro-2,2-dimethyltaurine in adenovirus type 5. Thereby, chlorination of the surface proteins is the first step, which can be assumed to impact their function and therefore the attachment of viruses to body cells. The multiple sites of chlorination of tyrosine, phenylalanine, and tryptophan and oxidation of methionine by NCT in the spike protein found in the present study clearly confirm this principle in SARS-CoV-2, too. Further targets are generally mainly thio groups and amino groups. Actually, we found oxidation of cysteine and methionine in the 3C-like proteinase of the virus besides chlorination of tyrosine and histidine, which underlines the attack of NCT at multiple proteins. Despite the occurrence of 40 cysteines in the spike protein (FIG. 4), no oxidation of them by NCT could be detected. A realistic explanation may be that they cannot be reached by NCT within the protein, which is underlined by their occurrence in part as disulfides (cystine).

Oxidation and chlorination of virulence factors of different pathogens by NCT and analogue chloramines with the consequence of their inactivation has been also shown for shigatoxin of *Escherichia coli,* several toxins of *Staphylococcus aureus,* aspartyl proteinases of *Candida* spp. and gliotoxin of *Aspergillus fumigatus.* This indicates that inactivation of key proteins of all kinds of pathogens is a central principle of the antimicrobial action of NCT and may underline such a function in innate immunity besides its anti-inflammatory one.

Accordingly, the activity of NCT against the SARS-CoV-2 variants of concern was almost identical to that against the wild type. This result means that mutations in the protein sequence have no influence on the susceptibility of the virus to NCT. Similarly, multiresistance of bacteria and fungi against antibiotics and antifungals does not play a role for their susceptibility to NCT. As a further consequence, NCT has not only virucidal activity against enveloped viruses (herpes virus type 1 and 2, human immunodeficiency virus 1, and the viruses of the present study), but also non-enveloped ones. From the latter, a panel of adenoviruses has been tested mainly due to their importance in epidemic keratoconjunctivitis. Similar to other active halogen compounds and other antiseptics such as tensidic compounds, adenoviruses are slightly less sensitive to NCT than the enveloped viruses. Nevertheless, efficacy of NCT in vivo against adenoviruses in epidemic keratoconjunctivitis has been proven in the New Zealand White rabbit ocular model and in a phase II study in humans. Application of NCT had a curative effect in a patient suffering from therapy-refractory herpes zoster infection in the upper thoracic area.

It must be taken into account that organic substances are omnipresent in vivo (in all human body fluids and tissues), and therefore we performed a part of the inactivation assays in the presence of organic matter as well. The results of clearly show an enhancement of the virucidal activity of NCT in the presence of 5.0% peptone, which in the first view appears surprising since active chlorine compounds underlie a decrease of their oxidation capacity by chlorine-reducing substances of such organic load. With NCT as a low-reactive chloramine compound, however, transchlorination as one of the reaction mechanisms becomes important. Thereby, amongst others, monochloramine (NH2Cl) is formed in equilibrium from NCT and ammonium chloride.

Cl—HN—CH2-CH2-SO3-+NH4Cl↔H2N—CH2-CH2-SO3-+NH2Cl+H++Cl

NCT+Ammonium Chloride↔Taurine Monochloramine

Monochloramine is more lipophilic than NCT and penetrates microorganisms more easily, which leads to enhanced inactivation by the reaction just mentioned. The stronger activity of NCT in the presence of fluids containing proteinaceous material is a general principle observed in different compositions, such as artificial sputum medium, different body fluids, peptone, and plasma for bacteria and fungi. In the present study, it has been confirmed for viruses for the first time, too. The discrepancy between the incubation time of 15 min and of 10 min or less needed for a significant viral reduction in buffer solution in different tests may be explained by the presence of 1.0% FCS in the tests and organic matter in the presence of Vero cells. In agreement with these results, enhancement of the bactericidal and fungicidal activity of NCT in the presence of different lung epithelial cells was observed recently.

Enhancement of antimicrobial and antiviral activity by organic material is of practical relevance for topical treatment of infections with NCT, for instance bronchopulmonary ones. The concentration of active chlorine after the end of an inhalation of 1.0% NCT decreases to traces within 1 min and vanishes completely after further 10 min. Inhalation for 10 min is feasible and well tolerated, and within this time an impact on SARS-CoV-2 and on other viruses can be expected in vivo, too, but remains to be evaluated in respective clinical studies.

Also of practical relevance is the fact that NCT has broad-spectrum activity against viruses, including important representatives relevant for bronchopulmonary infections (SARS-CoV-2, influenza viruses, RSV). Of note, even different variants of the viruses with concerning phenotypes such as increased spread or virulence are similarly susceptible due to the unspecific, oxidizing and chlorinating mechanism of action of NCT. Topical treatment of all these virus infections by inhaled NCT without the necessity of a diagnosis of the specific virus at hand is conceivable and should urgently be investigated in clinical studies. Notably, the activity of NCT against bacteria and fungi, including multi-resistant ones, may prevent super- and secondary infections, which are a considerable problem in COVID-19 patients as well. In addition, the anti-inflammatory activity of NCT might have the potential to influence the aggressive inflammatory response by downregulating the "cytokine storm" and prevent airway damage in severe ill patients with SARS-CoV-2 infection. Further advantages of NCT would be high safety and high tolerability by human tissue, absence of systemic absorption, of systemic adverse effects, of systemic interaction with other medications, and of resistance development because of the oxidizing and chlorinating mechanism of action.

Conclusion. NCT demonstrated rapid activity against SARS-CoV-2, influenza A viruses, and RSV at a therapeutic concentration of 1.0% that can be safely inhaled. The molecular mechanism of action consists of oxidative attack at multiple sites of essential viral proteins, which excludes development of resistance and maintains virucidal activity against virus variants. The activity is enhanced by an organic environment, which is omnipresent in human body fluids and tissues in vivo. Clinical efficacy of NCT in viral bronchopulmonary infections are presented in the following examples herein.

Treatment

NCT has been found to be useful in the treatment of COVID-19 (infection with SARS-CoV-2). Therefore, a particularly preferred embodiment of the invention is an alkali salt of N-Chlorotaurine, preferably NCT-Na, for use in the treatment of COVID-19 or infections with derivatives of SARS-CoV-2.

NCT can be administered as a nasal/throat spray/rinse solution. The solution here consists of about 0.1% to about 5% NCT in a suitable solvent, a preferred embodiment is distilled water. A solution of about 1% NCT in distilled water is a particularly preferred embodiment.

In the first stages of disease, which is infection of the nose and throat, 1% NCT aqueous solution may be used as a nose spray (two to three puffs (about 0.1 ml/puff) per nostril during forced nasal inspiration) and/or throat spray (three to five puffs (about 0.1 ml/puff) in the back of the mouth to the throat). Alternatively, 1% NCT aqueous solution may be used as a nasal rinse (10 ml to 20 ml instilled for 30 seconds up to 1 minute) and/or throat gargling solution (10 ml to 20 ml for 30 seconds up to 1 minute). This may be repeated at least three times per day, and more often is even better (about 5 times a day) in the acute phase.

Early application is the best treatment strategy upon viral infections of the nose and/or throat region. Apply repeatedly and immediately upon the first itching in the nose or first scratching in the throat to inhibit the spread of the infection instantaneously or to attenuate the infection. If there is already a full infection established with marked symptoms, the application has demonstrated an attenuation of the symptoms. Treatment should be done for a few days until the pain and strong exudation goes away.

NCT must not be mixed with other substances in one solution. The patient should not eat or drink anything for at least 10 minutes, to avoid an impact on the activity of NCT since nutrition and fluids may inactivate NCT. There should be a period of at least 30 min to topical application of other substances to avoid mutual inactivation.

This treatment can markedly attenuate the course of viral flu-like infections. It has been observed to inhibit the occurrence of bronchitis in patients who always get bronchitis upon upper airway infections after a few days. The same inhibition has also been observed in COVID-19 patients, which means avoidance of the second stage of disease, which is development of pneumonia.

NCT-Na can also be administered as an inhalation solution. The solution here consists of about 0.1% to about 1% NCT-Na in a suitable solvent, a preferred embodiment is distilled water. A solution of about 1% NCT-Na in distilled water is a particularly preferred embodiment.

This solution is inhaled through a nebulizer (e.g. Pari Boy, Multisonic ultrasonic nebulizer, Akita Jet, Aero Eclipse II) until the symptoms disappear. Depending on the nebulizer, single doses of 3-10 ml of the solution can be administered, and about 3 ml is a preferred embodiment. These single doses are administered 1 to 10 times a day, and a preferred embodiment is 3 times a day.

Nebulizer: The size of the droplets must be sufficiently small in pneumonia (e.g. Covid-19), i.e. smaller than 5 micrometers. (Mass Median Aerodynamic Diameter MMAD<5 μm). If a deposition in the bronchi is desired, larger droplet size may be used.

Patients in the acute phase with pneumonia/bronchitis may inhale 2 to 3 times daily with 3 ml to 5 ml 1% NCT solution in the nebulizer for 10 min. Interval to possible other inhalations at least 15 min in case of 0.9% saline and 30 min in case of other inhaled medications.

May not mix with other drugs because of the oxidizing activity and mutual inactivation. Clean the reservoir of the nebulizer with water from other medications used previously.

Prophylaxis

NCT may also be applied as nose/throat spray/rinse solution for prevention/prophylaxis of worsening or contagiousity to other persons. Even in case of low or no symptoms, 1% NCT aqueous solution may be used as a nose spray (two-three puffs (about 0.1 ml/puff) per nostril during forced nasal inspiration) and/or throat spray (three-four puffs (about 0.1 ml/puff) in the back of the mouth to the throat). Alternatively, 1% NCT aqueous solution may be used as a nasal rinse (10 ml to 20 ml instilled for 30 seconds up to 1 minute) and/or throat gargling solution (10 ml to 20 ml for 30 seconds up to 1 minute). This may be repeated at least two times per day or after close contact with other persons.

Of particular note, several cases have been observed where persons remained negative upon use of the 1% NCT nasal spray despite a close contact to COVID-19 positive persons, and even where other contact persons not using the 1% NCT nasal spray became positive.

Viral Load

One main aim is to reduce the viral load in the upper airways. It is well known that ct values in the PCR above about 30 cycles lead to positivity in cell culture only in part. Above 35 cycles all cell cultures are negative. However, these numbers are variable since the PCRs of different labs are hardly well comparable.

NCT spray application leads to a decrease of infectiousity by decreasing of viral load compared to untreated controls, directly inactivating a partial number of the viruses, and attenuating a partial number of the viruses.

With bacteria and fungi, a short, sublethal incubation time of bacteria and fungi in NCT leads to a clear loss of their virulence in mice and moth larvae. At least one reason is immediate chlorination of the surface, which leads to damage of surface proteins and a lag of regrowth (postantibiotic/postantiseptic effect). The pathogens need the lag time to restore their surface and virulence factors to recover. This principle is the same for viruses: NCT will oxidize and chlorinate the surface proteins of SARS-CoV-2, too, which will block attachment to cells. Also, the targets for the virus on the body cell surface are oxidized and chlorinated by NCT, so it has an immediate effect from both sides.

The Invention is Further Explicated by Means of the Following Examples.

Example 1. Treatment of COVD-19 patient with 1% NCT nasal spray, throat gargling solution, and inhalation.

Male patient in early 50s, without any underlying conditions. (Day 0): Symptoms onset: morning sweating and feeling sick, nasal secretion amplified, incipiating sore throat. Immediately began treatment with 1% NCT nasal spray (2-3 puffs (0.1 ml/puff) per nostril) and gargling solution (10 ml-20 ml for 30 sec-60 sec). Two hours later (about 9:30 AM), took smear of nose and throat in the morning, both positive in PCR; positive after 30-32 cycles PCR. Continued 1% NCT nasal spray and gargling solution (3×daily); inhaled 5 ml 1% NCT (2×daily) around noon and evening for 15 min. Sore throat did not occur, secretion became significantly lower. Redness of throat was very low. Feeling sick and weakness between 11:00 AM and 2:00 PM. (Day 1): Sweating and feeling sick in the morning, no more secretion, only from time to time still slight scratching of the throat with low cough irritation. Around 10:00 AM, continued 1% NCT nasal spray and gargling solution (3×daily); inhaled 5 ml 1% NCT (2×daily. Again temperature dropped in the morning. Did not lay down to rest during the day. (Day 2): Some night sweat; no respiratory problems, but muscle pain at the back; Continued 1% NCT nasal spray and gargling solution (3×daily); inhaled 5 ml 1% NCT (2×daily). Temperature normal. (Day 3): Some night sweat; no respiratory problems, muscle pain practically gone; temperature normal. Stopped 1% NCT therapy due to lack of symptoms. Throat swab made at 10:00 PM, in the morning both nostrils added. Result of the test two days later were positive after 25 cycles PCR. (Day 4): no complaints; (Day 5): no complaints; (Day 6): no discomfort: nose-throat smear at 11:00 AM. Test results on the same day: still positive after 27 cycles PCR. (Day 7): no complaints; (Day 8): no complaints; (Day 9): no complaints; (Day 10): no complaints; (Day 11): end of quarantine; no complaints; patient embarked on a winter cross-country mountain skiing tour. (Day 13): throat and nasal smear control PCR: weakly positive after 36.5 cycles (curve weak; max cycle number 45); (Day 19): throat and nasal smear control PCR: negative.

Discussion. Patient began 1% NCT nasal spray and throat gargling therapy after the onset of symptoms on the morning of Day 0, but two-hours before taking first COVID-19 PCR test smear (30-32 cycles). Symptoms and NCT therapy stopped by day 3. However, the second PCR test smear was taken on the evening Day 3 (after the patient had stopped therapy) and was higher (25 cycles). A reasonable explanation for this result is arguably that the initial NCT therapy two-hours before the first PCR effectively reduced the viral load, whereas the stoppage of NCT therapy approximately 24 hours before the second PCR did not effectively reduce the viral load.

Example 2. Treatment of COVD-19 patient with 1% NCT nasal spray and throat gargling solution and prophylaxis of family members with 1% NCT.

Male patient age in early 50s. His only symptom was a slight rhinitis. (Day 0): Swab with a PCR ct value of 14 cycles before NCT treatment on the first day. Start of 1% NCT therapy with nose spray (2-3 puffs (0.1 ml/puff) per nostril) and gargling solution (10 ml-20 ml for 30 sec-60 sec) about 6 hours later in the evening. (Day 1): Continuation of 1% NCT therapy (3× daily). Swab in the evening of the next day two hours after dosing: PCR ct value 20-22 cycles. Hardly any more symptoms. Continuation of 1% NCT therapy. (Day 2): Continuation of 1% NCT therapy. (Day 3): Continuation of 1% NCT therapy. (Day 4): Swab 3 days later in the evening of day 4: PCR ct value 31-34 cycles. No more symptoms. Continuation of 1% NCT therapy. (Day 5): Continuation of 1% NCT therapy on the whole next day. (Day 6): Swab in the morning of Day 6, which was 14 hours after the last dosing of NCT: PCR ct value equal 31-34 cycles. Stop of 1% NCT therapy due to this low value. No more symptoms, back to work after 10 days quarantine, swab negative.

Patient's wife and his three teenagers all residing in the same home also used 1% NCT nose and throat spray for 3 times daily as a prophylaxis, and they remained negative.

Example 3. Treatment of COVD-19 patient with 1% NCT nasal spray.

Male patient age 45. Previous Medical History of Mild Cardiomyopathy (10 years before) and Miocarditis (4 years before). (Day 0): early morning aches and muscle pain. Minor sore throat and nasal secretion. Feeling tired, generally ill and weak throughout the day. (Day 1): early morning aches, muscle pain, sweating. Minor sore throat and nasal secretion and cough. Feeling ill, tired, and weak throughout the day. Started to take Vitamin C, Zicam. Tested Positive for COVID-19 using rapid test. (Day 2): early morning aches, severe sweating (3 am) in morning. Increased cough and mucus secretion. Sam feeling extremely ill, tired, pale, weak and experiencing upper back pain. 8:30 am—feat and palm sweats, uncontrollable chills and body shakes. Pulse drops to 40 bpm and admitted to ER. Given IV fluids, EKG, Chest X-Ray, and lab work completed. Lab work showed dehydration, IVF given, then released. (Day 3): experience loss of taste and smell, bad headaches, exhaustion. Very weak and tired. Continued back aches. (Day 4): bad headaches continue. Overall feeling of tiredness, nasal congestion, small cough, some mucus. (Day 5): bad headaches continue. Overall feeling of tiredness with periods of exhaustion. Nasal congestion with minor cough and mucus secretion. Began taking 1% NCT at 8 pm via nasal spray 2 puffs (0.1 ml/puff) in each nostril. Within 30 minutes nasal passages cleared and nasal secretion dried up. (Day 6): Continue general malaise throughout the day, headaches, overall feeling of weakness. Took NCT nasal spray 3× in each nostril at 8 am, 2 pm and 9 pm. (Day 7): Took NCT nasal spray 3× in each nostril at 8 am, 2 pm and 9 pm. Feeling better with more energy in the morning but experience tiredness by mid-day. Nasal passages and sinus clear, minor cough, no secretion. (Day 8): Took NCT nasal spray 3× in each nostril at 8 am, 2 pm and 9 pm. Feeling better with more energy in the morning but experience tiredness by mid-day. Nasal passages and clear, minor cough, no secretion. (Day 9): Took NCT nasal spray 3× in each nostril at 8 am, 2 pm and 9 pm. Feeling better with more energy in the morning but experience tiredness by mid-day. Nasal passages and clear, minor cough, no secretion. Night-time sweats. (Day 10): Took NCT nasal spray 3× in each nostril at 8 am, 2 pm and 9 pm. Feeling better with more energy with periods of tiredness. No cough or nasal secretion. (Day 11): Feeling better with more energy. Slight headaches come and go but overall better feeling. Stopped taking NCT. (Day 12): Feeling better with more energy. Slight headaches come and go but overall better feeling. (Day 13): Feeling better with more energy. Slight headaches come and go but overall better feeling.

Discussion. Overall, it took patient full three weeks to fully recover from COVID-19. By week three headaches were not as bad, and generally experience more energy throughout the day. By the end of week three slowly began to start exercise again. Patient reported that he started feeling better within minutes of beginning NCT therapy, and he felt that this was the turning point towards his recovery.

Example 4. Treatment of COVD-19 patient with 1% NCT nasal/throat spray and prophylaxis of spouse with 1% NCT.

Male patient age 32 years with previous history of smoking cigarettes (quit 1 year ago). (Day 0): tested positive for COVID-19 (rapid test). (Day 3): symptoms of stuffy nose and sore throat. (Day 4): Began taking 1% NCT therapy, i.e., nasal spray (3× (0.1 ml/puff) per nostril) and throat spray (5× puffs (0.1 ml/puff)) in the back of the mouth to the throat; dose time and symptoms: 11:00 AM—Sore throat, mucus 4:30 PM—Sore throat, less mucus 10:25 PM—Some dry mucus 2:15 AM—Less sore throat, dry mucus. (Day 5): dose time and symptoms: 12:05 PM—Sore throat, mostly clear nasal passages; 4:30 PM—Sore throat, minor mucus 2:00 AM—Minor symptoms (didn't write this one down, but patient thought he took a dose at this time so he included it). (Day 6): dose time and symptoms: 12:05 PM—Minor soreness in throat, mucus 8:05 PM—Mild sore throat and mild mucus 12:05 AM Mild sore throat and mild mucus. (Day 7): dose time and symptoms: 2:05 PM—Sore throat, minor mucus 5:15 PM—Minor soreness in throat 8:25 PM—Minor sore throat, minor mucus 12:43 AM—No symptoms. (Day 8): dose time and symptoms: 1:13 PM—Minor sore throat 7:17 PM—Minor sore throat 3:43 AM—No symptoms. (Day 9): dose time and symptoms: 12:30 PM—Minor mucus 4:48 PM—No symptoms 9:00 PM—No symptoms. (Day 10): dose time and symptoms: 10:57 PM—No symptoms.

Spouse, Female age 32. (Day 7 of husband's infection) dose time and symptoms: 2:10 PM—No symptoms 8:25 PM—No symptoms. (Day 8 of husband's infection) dose time and symptoms: 2:40 PM—No symptoms 11:30 PM—No symptoms. (Day 9 of husband's infection) dose time and symptoms: 11:10 AM—No symptoms 7:15 P. No symptoms.

Example 5. Treatment of Patients who suffer from COVID-19, with NCT solution for inhalation.

The effect of an inhalation solution of NCT-Na is tested in patients who suffer from COVID-19 (infection with SARS-CoV-2). The solution consists of 1% NCT sodium in distilled water.

Eight hospitalized patients inhaled 3 ml of this solution 3 times a day for 1 week to 9 days via a nebulizer, and were then able to leave the hospital with survived illness and symptom-free or largely symptom-free.

Another 20 hospitalized patients suffering from COVID-19 were concurrently undergoing the same treatment, during which there was no progression of the disease and lung failure was avoided.

The forgoing examples are illustrative only, and not meant to limit the scope of the inventions claimed herein.

What is claimed is:

1. A method of treating or preventing a viral coronavirus respiratory infection in a mammal, said method consisting essentially of administering a therapeutically effective amount of N-chlorotaurine.

2. The method according to claim 1, wherein said coronavirus comprises severe acute respiratory syndrome coronavirus 2 (SARS-COV-2), or variants thereof.

3. The method according to claim 2, wherein said therapeutically effective amount of N-chlorotaurine comprises about a 0.1% to 1% solution of N-chlorotaurine.

4. The method according to claim 3, wherein said therapeutically effective amount of N-chlorotaurine comprises about a 1.0% solution of N-chlorotaurine in water.

5. The method according to claim 4, wherein said administering a therapeutically effective amount of N-chlorotaurine is selected from a group consisting of nasal administration, oral administration, and inhalation.

6. The method according to claim 5, wherein said nasal administration comprises administration by nasal spray to the nostrils.

7. The method according to claim 6, wherein said therapeutically effective amount of N-chlorotaurine comprises a dosage of about 0.1 ml to 0.3 ml per administration to each of said nostrils, administered about 2 to 4 times per day.

8. The method according to claim 5, wherein said oral administration comprises administration by oral spray to the throat.

9. The method according to claim 8, wherein said therapeutically effective amount of N-chlorotaurine comprises a dosage of about 0.3 ml to 0.6 ml per administration to said throat, administered about 2 to 4 times per day.

10. The method according to claim 5, wherein said therapeutically effective amount of N-chlorotaurine comprises administration by inhalation to the lungs.

11. The method according to claim 10, wherein said inhalation comprises administration by nebulizer to said lungs.

12. The method according to claim 11, wherein said therapeutically effective amount of N-chlorotaurine comprises a dosage of about 2 ml to 5 ml per administration to said lungs, administered about 2 to 4 times per day.

\* \* \* \* \*